United States Patent
Barth et al.

(10) Patent No.: US 9,872,904 B2
(45) Date of Patent: Jan. 23, 2018

(54) PHOTOIMMUNOCONJUGATES FOR USE IN PHOTODYNAMIC THERAPY

(75) Inventors: Stefan Barth, Munich (DE); Mehmet K. Tur, Aachen (DE); Ahmad Hussain, Aachen (DE)

(73) Assignees: Fraunhofer-Gesellschaft zur Foerderung der angewandten Forschung e.V., Munich (DE); Rheinisch-Westfaelische Technische Hochschule Aachen, Aachen (DE)

( * ) Notice: Subject to any disclaimer, the term of this patent is extended or adjusted under 35 U.S.C. 154(b) by 305 days.

(21) Appl. No.: 14/381,386

(22) PCT Filed: Mar. 21, 2012

(86) PCT No.: PCT/EP2012/055022
§ 371 (c)(1),
(2), (4) Date: Jan. 16, 2015

(87) PCT Pub. No.: WO2013/139391
PCT Pub. Date: Sep. 26, 2013

(65) Prior Publication Data
US 2015/0140022 A1    May 21, 2015

(51) Int. Cl.
| | |
|---|---|
| *A61K 47/64* | (2017.01) |
| *A61K 47/48* | (2006.01) |
| *C07K 16/28* | (2006.01) |
| *G01N 33/532* | (2006.01) |
| *A61K 41/00* | (2006.01) |
| *C07K 16/30* | (2006.01) |
| *C12N 9/10* | (2006.01) |
| *A61K 47/60* | (2017.01) |
| *A61K 47/68* | (2017.01) |

(52) U.S. Cl.
CPC .......... *A61K 41/0071* (2013.01); *A61K 47/60* (2017.08); *A61K 47/64* (2017.08); *A61K 47/6849* (2017.08); *C07K 16/2863* (2013.01); *C07K 16/2878* (2013.01); *C07K 16/30* (2013.01); *C12N 9/1007* (2013.01); *C07K 2317/622* (2013.01); *C12Y 201/01063* (2013.01)

(58) Field of Classification Search
CPC .......... C07K 2319/00; C07K 2319/60; C07K 16/2863; C12N 9/1007; C12N 9/1085; C12N 2529/10; A61K 49/0026; A61K 41/0071; A61K 41/0076; A61K 47/6849; C12Y 201/01063; G01N 33/532
See application file for complete search history.

(56) References Cited

U.S. PATENT DOCUMENTS 6,936,469 B2    8/2005    deJong et al.

FOREIGN PATENT DOCUMENTS

| | | |
|---|---|---|
| EP | 1 882 688 A1 | 1/2008 |
| JP | 2007-525410 A | 9/2007 |
| WO | WO-95/25167 A1 | 9/1995 |
| WO | WO-2004/065547 A2 | 8/2004 |
| WO | WO-2009/013359 A2 | 1/2009 |
| WO | WO-2009/013359 A3 | 1/2009 |

OTHER PUBLICATIONS

Keppler et al., Methods 32: 437-444, 2004.*
Hussain et al., Bioconjugate Chemistry 22: 2487-2495, Dec. 11, 2011.*
Yu et al., Investigative Ophthalmology & Visual Science 49(2): 522-527, Feb. 2008.*
Cochran et al., J. Immunol. Meth. 287: 147-158, 2004.*
Colman P. M., Research in Immunology, 145:33-36, 1994.*
Wu et al., J Mol Biol 294: 151-162, 1999.*
Dufner et al., Trends Biotechnol 24(11): 523-529, 2006.*
Kappler et al., Biotechniques 41(2): 167-175, 2006.*
Adams et al., Monoclonal antibody therapy of cancer. Nat. Biotechnol. 23, 1147-1157 (2005).
Bhatti, M. et al. Targeted photodynamic therapy with multiply-loaded recom-binant antibody fragments. Int J Cancer 1,122:1155-63 (2008).
Cai, K. et al. Relationship between induction of phosphorylated H2AX and sur-vival in breast cancer cells exposed to mln-DTPA-hEGF. 3 Nucl Med. 49, 1353-1361 (2008).
Castano et al., Mechanisms in photodynamic therapy: part one-photosensitizers, photochemistry and cellular localization. Photodiagnosis and Photodynamic Therapy 1, 279-293 (2004).
Douillard, S., Olivier, D. & Patrice, T. In vitro and in vivo evaluation of Radachlorin® sensitizer for photodynamic therapy. Photochem Photobiol. Sci 8, 405-413 (2009).
Gamou et al., Different responses to EGF in two human carcinoma cell lines, A431 and UCVA-1, possessing high numbers of EGF re-ceptors. Mal. Cell. Endocrinol. 37, 205-213 (1986).
Hamblett, K.J. et al. Effects of drug loading on the antitumor activity of a monoclonal antibody drug conjugate. Clin. Cancer Res. 10, 7063-7070 (2004).
Huang, Z. A Review of Progress in Clinical Photodynamic Therapy. Technol Cancer Res Treat. 4, 283-293 (2005).
Jeger, S. et al. Site-Specific and Stoichiometric Modification of Antibodies by Bacterial Transglutaminase. Angew. Chem. Int. Ed. 49, 9995-9997 (2010).
Junutula, J.R. et al. Site-specific conjugation of a cytotoxic drug to an anti-body improves the therapeutic index. Nat. Biotechnol. 26, 925-932 (2008).

(Continued)

*Primary Examiner* — Phuong Huynh
(74) *Attorney, Agent, or Firm* — Venable LLP; Keith G. Haddaway; Kerri M. Patterson (57) ABSTRACT

A compound comprising
  a photosensitizer covalently coupled to
  a protein selected from the group consisting of antibodies or their derivatives or fragments thereof, synthetic peptides such as scFv, mimotopes
  which bind CD antigens, cytokine receptors, interleukin receptors, hormone receptors, growth factor receptors, more particularly tyrosine kinase growth factor receptor of the ErbB family, wherein
  the photosensitizer is coupled to the binding protein via O6-alkylguanine-DNA alkyltransferase (hAGTm), a modified human DNA repair protein.

22 Claims, 5 Drawing Sheets

(56) References Cited

OTHER PUBLICATIONS

Kampmeier, F. et al. Rapid optical imaging of EGF receptor expression with a single-chain antibody SNAP-tag fusion protein. Eur. 3. Nucl. Med. Mol. Imag-ing 37, 1926-1934 (2010).

Kampmeier F. et al. Site-specific, covalent labeling of recombinant antibody fragments via fusion to an engineered version of 6-Oalkylguanine DNA alkyltransferase. Bioconjug Chem. 20, 1010-1015 (2009).

Nida et al., Fluorescent nanocrystals for use in early cervical cancer detection. Gynecolog-ic Oncology 99, 89-94 (2005).

Olivo et al., Target-ed Therapy of Cancer Using Photodynamic Therapy in Combination with Multi-faceted Anti-Tumor Modalities. Pharmaceuticals 3, 1507-1529 (2010).

Palumbo, G. Photodynamic therapy and cancer: a brief sightseeing tour. Ex-pert Opin. Drug Deliv. 4, 131-148 (2007).

Van Dongen et al., Photosensitizer-antibody conjugates for detection and therapy of cancer. Adv. Drug. Delivery. Rev. 56, 31-52 (2004).

Ogura et al., Expected Materials for the Features, Jun. 10, 2002, vol. 2, No. 6, pp. 30-35 (9 pages).

Fujita et al., Photodynamic effect of cholorin e6-immunoconjugate, Proceedings of the 78th Annual Spring Meeting of the Chemical Society of Japan, Mar. 2000, p. 708 (5 pages).

Office Action in Japanese Application 2015-500780, dated Feb. 9, 2016.

Nela Malatesti et al., "Synthesis and in vitro investigation of cationic 5,15-diphenyl porphyrin-monoclonal antibody conjugates as targeted photodynamic sensitisers", International Journal of Oncology, vol. 28, No. 6, pp. 1561-1569 (Jun. 1, 2006).

Gronemeyer et al., "Directed evolution of $O^6$-alkylguanine-DNA alkyltransferase for applications in protein labeling", Protein Engineering Design & Selection, vol. 19, No. 7, pp. 309-316 (Jan. 1, 2006).

Keppler et al., "Labeling of fusion proteins with synthetic fluorophores in live cells", Proceedings of the National Academy of Sciences, vol. 101, No. 27, pp. 9955-9959, XP002462236 (Jul. 6, 2004).

Barth et al., "Ki-4(scFv)-ETA, a new recombinant anti-CD30 immunotoxin with highly specific cytotoxic activity against disseminated Hodgkin tumors in SCID mice", The American Society of Hematology, vol. 95, No. 12, pp. 3909-3914, XP002245489 (Jun. 15, 2000).

International Search Report dated Oct. 24, 2012 in PCT/EP2012/055022.

Office Action dated Sep. 13, 2016 for European Patent Application No. 12 709 646.9-1453.

Hussain, A. F., Kampmeier, F., von Felbert, V., Merk, H., Tur, M. K., and Barth, S., SNAP-Tag Technology Mediates Site Specific Conjugation of Antibody Fragments with a Photosensitizer and Improves Target Specific Phototoxicity in Tumor Cells, Bioconjugate Chemistry, 2011, vol. 22, pp. 2487-2495, ACS Publications, American Chemical Society.

* cited by examiner

PHOTOIMMUNOCONJUGATES FOR USE IN PHOTODYNAMIC THERAPY

This application is a U.S. National Stage of International Application No. PCT/EP2012/055022, filed Mar. 21, 2012, which is incorporated by reference herein in its entirety.

FIELD OF THE INVENTION

Photodynamic therapy (PDT) is a promising and minimally invasive approach for the treatment of cancer. Following the introduction of improved photosensitizers and clinical application protocols, several FDA-approved PDT drugs have become available and others are in various stages of preclinical and clinical development[1]. The photosensitizing agent can exert its effect when activated by non-hazardous light directly, by becoming cytotoxic, or indirectly, by initiating the in situ production of toxic free radicals or reactive oxygen species (ROS). These processes cause damage to cells and ultimately induce cell death by apoptosis or necrosis[2]. The site of cellular damage depends on the photosensitizer type, the incubation period and the mode of delivery. Hydrophobic photosensitizers tend to damage cell membranes, whereas cationic photosensitizers accumulate within membrane vesicles such as mitochondria and cause local damage[3].

One of the greatest challenges in PDT is the lack of targeting specificity. Photosensitizers damage healthy tissue as well as tumor tissue after activation by light, and this can result in prolonged skin photosensitivity[4]. To increase the specificity of PDT, photosensitizers have been conjugated to tumor-specific monoclonal antibodies or single chain antibody fragments (scFv), resulting in so-called photoimmunoconjugates that deliver the photosensitizer directly to the tumor tissue. This approach is known as photoimmunotherapy (PIT)[5]. Standard coupling reactions are unsuitable for the conjugation of photosensitizers and antibodies because there is no reliable way to ensure that antibody-photosensitizer conjugates are produced in the optimal stoichiometric ratio[6]. Furthermore, the chemical properties of the photosensitizer (e.g. hydrophobicity and the number and arrangement of charged groups) can alter the pharmacokinetic properties and biodistribution of the antibody, finally causing non-specific binding and internalization behavior. Random conjugation can also induce the self-quenching of photosensitizer-excited states, thus reducing photodynamic activity[5]. More controlled conjugation reactions are therefore required to overcome these limitations.

One of the main drawbacks of PDT is the non-selective effect of activated photosensitizers, which tend to damage healthy as well as tumor cells. Targeted therapy using antibodies has revolutionized cancer treatment and several antibodies that bind to tumor cell antigens have achieved blockbuster status. The efficacy of therapeutic antibodies can be improved by their covalent conjugation to additional effector molecules (e.g. radio nuclides, drugs or toxins)[7], as this achieves selective delivery and should reduce the systemic toxicity traditionally associated with small molecule drugs[8]. The same principle can be applied to photosensitizers. Effector molecules are generally conjugated to antibodies using either the reduced sulfhydryl groups of cysteine residues or amino groups in lysine side chains. However, both methods yield heterogeneous products, comprising a mixture of conjugated antibodies with the effector attached at different sites, and a variable number of effectors attached to each antibody resulting in a range of molar rations and very different pharmacokinetic, efficacy and safety profiles.

Hamblett and colleagues[9] have studied the toxicity, pharmacokinetic properties and therapeutic efficacy of heterogeneous antibody-drug conjugates by purifying three antibody fractions containing two, four and eight conjugated molecules of monomethyl-auristatin E (MMAE). The fraction with eight MMAE groups was poorly tolerated and rapidly cleared compared to the other fractions, and demonstrated the lowest efficacy. This suggests that the key design parameter for antibody-drug conjugates is the number of drug molecules attached to the antibody. However, even purified antibodies carrying the same number of drug molecules still constitute a complex mixture because of the many alternative attachment sites. For example, there are approximately 40 lysine residues in a typical antibody, potentially resulting in more than one million different conjugated antibody species. Similarly, there are between one and eight cysteine residues, typically generating approximately 100 different conjugated variants. Each version of the antibody-drug conjugant typically displays a unique and unpredictable pharmacokinetic profile[9].

SUMMARY OF THE INVENTION

Cancer cells can be killed by photosensitizing agents that induce toxic effects when exposed to non-hazardous light, but this also causes significant damage to surrounding healthy cells. The specificity of photodynamic therapy can be increased by conjugating photosensitizing agents to antibodies and antibody fragments that bind specifically to tumor-associated cell surface antigens. However, standard conjugation reactions produce heterogeneous products whose targeting specificity and spectroscopic properties can be compromised.

In this invention, an antibody fragment (scFv-425) has been used that binds to the epidermal growth factor receptor (EGFR) as a model to investigate the use of SNAP-tag fusions as an improved conjugation strategy. The scFv-425-SNAP-tag fusion protein allowed the specific conjugation of a photosensitizer, such as chlorin e6, modified with O(6)-benzylguanine, generating a homogeneous product that was delivered specifically to EGFR+ cancer cells and resulted in significant, tumor cell-specific cytotoxicity. The impact of our results on the development of photodynamic therapy is discussed.

The present invention provides a compound comprising a photosensitizer covalently coupled to a binding structure selected from the group consisting of antibodies or their derivatives or fragments thereof, synthetic peptides such as scFv, mimotopes, which binding structure binds to CD antigens, cytokine receptors, interleukin receptors, hormone receptors, growth factor receptors, more particularly tyrosine kinase growth factor receptor of the ErbB family, wherein the photosensitizer is coupled to the internalizing receptor binding protein via the modified human DNA repair protein O6-alkylguanine-DNA alkyltransferase (hAGTm).

In one embodiment of the present invention the epidermal growth factor receptor binding protein is a scFv antibody fragment, in particular the scFv antibody fragment of the Seq ID No 1, encoded by the polynucleotide sequence of Seq ID No 2.

In another embodiment of the invention the compound of the invention comprises or has the amino acid sequence Seq ID No 3, encoded by the polynucleotide sequence of Seq ID No 4.

In yet another embodiment of the compound of the invention the photosensitizer is coupled at the active site of the O6-alkylguanine-DNA alkyltransferase.

In the compound of the invention the photosensitizer is selected from the group consisting of porphyrins, chlorophylls and dyes having photosensitizing power.

Subject matter of the invention is also a compound devoid of a photosensitizer. The compound comprises a binding protein selected from the group consisting of antibodies or their derivatives or fragments thereof, synthetic peptides such as scFv, mimotopes, which binding protein binds CD antigens, cytokine receptors, interleukin receptors, hormone receptors, growth factor receptors, more particularly tyrosine kinase growth factor receptor of the ErbB family, which is covalently coupled to a modified human DNA repair protein called O6-alkylguanine-DNA alkyltransferase (hAGTm)

In particular the binding protein is an scFv antibody fragment, in particular the scFv antibody fragment of the Seq ID No 1 and/or Seq ID No 3. This compound can be encoded by a polynucleotide having the sequence of Seq ID NO 2 and/or Seq ID No 4. The specific embodiments bind to tyrosine kinase growth factor receptor of the ErbB family.

A specific embodiment of the compound is encoded by the polynucleotide of the nucleotide sequence of Seq ID No 5.

Another subject matter of the invention is a method for manufacturing the compound of the invention comprising the step of fusing O6-alkylguanine-DNA alkyltransferase (hAGTm) with a binding protein selected from the group consisting of antibodies or their derivatives or fragments thereof, synthetic peptides such as scFv, mimotopes, which binding protein binds CD antigens, cytokine receptors, interleukin receptors, hormone receptors, growth factor receptors, more particularly tyrosine kinase growth factor receptor of the ErbB family. In particular, the scFv-425 DNA sequence is inserted into the SifI and NotI-digested site of eukaryotic expression vector pMS-SNAP providing an N-terminal binding ligand (scFv-425) and a C-terminal SNAP-tag sequence.

In particular, a $His_6$ tag is also fused to the protein. The fused protein can be expressed in human cells in particular in embryonic kidney cell line such as HEK-293T cells (ATCC: CRL-11268) and purified using an affinity resin for the tag for example a Ni-NTA modified resin.

Also subject matter of the present invention is a porphyrin derivative of the formula Chlorin e6
($C_{34}H_{36}N_4O_6$)

wherein the carboxyl groups of the porphyrin photosensitizer, such as chlorin e6, are at least partially reacted to an activated ester or by a coupling agent, followed by reacting with O6-benzylguanine, O2-benzylcytosine or a coenzyme A (CoA).

In the method of the invention O6-benzylguanine, O2-benzylcytosine or a coenzyme A (CoA) a coupled to a linker molecule, such as PEG-24-$NH_2$ and/or the activated ester is formed by succinimides, such as NHS, or the coupling agent selected from the group consisting of a carbodiimide, such as EDC, EDAC and DCC.

Subject matter of the invention is also a medicament comprising the compounds of the invention and a pharmaceutically acceptable adjuvant for improving or render possible the pharmaceutical effect associated with the photoimmunotherapy.

The invention is also providing a use of the compounds of the invention for treating cancer by photoimmunotherapy.

The skilled person knows that the term "comprising" can be replaced by "consisting" without introducing new subject-matter extending beyond the matter disclosed herein.

The effects of the compound of the invention are demonstrated and more detailed described in the following by means of specific examples. The epidermal growth factor receptor (EGFR, erbB1, HER1), one of four member of the ErbB family of tyrosine kinase growth factor receptors, is overexpressed in approximately 30% of epithelial cancers and has thus become an attractive target for cancer immunotherapy[10]. The recombinant anti-EGFR antibody fragment scFv-425 binds to EGFR on the surface of cancer cells and induces receptor internalization efficiently[11]. scFv-425 is used as a model for the development of a new conjugation strategy to improve the specificity and efficacy of PIT. To achieve these aims the SNAP-tag technology has been used which is based on a 20-kD a modified human DNA repair protein called O6-alkylguanine-DNA alkyltransferase (hAGTm) that was initially developed for the site-specific labeling of antibodies with optically-active molecules[11]. The SNAP-tag allows efficient, covalent coupling to any substrate modified with the acceptor group O(6)-benzylguanine (BG). The SNAP-tag reacts with para-substituted BG derivatives by transferring the substituted benzyl group to its active site via a nucleophilic substitution reaction and releasing free guanine[11].

According to the invention a scFv-425-SNAP-tag fusion protein was designed and synthesised. A BG-modified chlorin e6 (Ce6) photosensitizer was delivered to EGFR+ cancer cells. The construct also included a linker region and 24 polyethylene glycol (PEG) chains to increase the distance between the photosensitizer and the protein. The BG-modified Ce6 was conjugated specifically and covalently to the scFv-425-SNAP-tag fusion protein with no detrimental impact on the binding and internalization activities of the antibody. Ce6 was delivered specifically to four EGFR+ carcinoma cell lines (A431, MDA-MB-231, MDA-MB-468 and SiHa) and resulted in significant, tumor cell-specific cytotoxicity.

DETAILED DESCRIPTION OF THE INVENTION

The present invention is further exemplary described in greater detail using Ce6 as photosensitizer and tyrosine kinase growth factor receptor of the ErbB family as the binding.

LEGENDS OF THE FIGURES

FIG. 1: Construction, expression and binding of the SNAP-tag fusion proteins. (a) Schematic diagram of the bicistronic eukaryotic expression cassettes for the recombinant SNAP-tag fusion protein. The pMS-scFV-425-SNAP vector encodes binding ligand (scFv-425) which is under the transcriptional control of the CMV promoter, and joined in-frame to the SNAP-tag. An immunoglobulin κ leader sequence (Ig-κ-L) facilitates protein secretion, and a TGA stop codon is placed immediately after the C-terminal $His_6$-tag. The expression cassettes for the control vector were the same as the PMS-scFv-425-SNAP but contain scFv-Ki4 instead of scFv-425 as a binding ligand. (b) Purification fractions of scFv-425-SNAP protein were separated by SDS-PAGE, and then stained with coomassie brilliant blue, (c) scFv-425-SNAP was incubated with BG-Vista green, proteins were visualized with UV light. M: Protein marker, 1: 3 µl of eluted scFv-425-SNAP with 250 mM Imidazol, 2: 1.5 µl of eluted scFv-425-SNAP with 250 mM Imidazol, 3: 10 µl of eluted scFv-425-SNAP with 40 mM Imidazol, 4: eluted protein with 10 mM Imidazol, 5: Flow through, 6: HEK-293T cells supernatant. Binding analysis of scFv-425-SNAP and scFv-Ki4-SNAP were assessed by flow cytometry using $EGFR^+$ A431 (d) and $EGFR^-$ L540 cells (e). Filled gray curves represent untreated cells. Cells were incubated with 0.5 µg/ml of the purified fusion protein scFv-425-SNAP (light gray curve) and Ki4-SNAP (black curve). As a secondary antibody a Penta-His Alexa Fluor 488 Conjugate (dilution 1/500) (Qiagen) was used. To exclude nonspecific staining of the anti-His Alexa Fluor 488 detection antibody, omission of the His-tagged fusion protein served as control (dotted black curves).

FIG. 2: Analysis of Ce6 photosensitizer by mass spectrometry before and after modification with benzylguanine (BG). (a) ESI mass spectrum of Ce6, $BG-PEG24-NH_2$, and BG-PEG24-Ce6. The top panel represents Ce6 (597.215 Da), the middle panel represents $BG-PEG24-NH_2$ (1398.761 Da) and the bottom panel represents BG-PEG24-Ce6 (1979.004 Da). (b) Coupling of BG-PEG24-Ce6 to scFv-425-SNAP. M, protein marker; 1, scFv-425-SNAP incubated with a 1.5-fold molar excess of BG-VistaGreen; 2, scFv-425-SNAP blocked with a 3-fold molar excess of bromothenylpteridine (BTP), incubated with BG-Ce6 for 2 h, and finally mixed with BG-VistaGreen; 3, scFv-425-SNAP incubated with a 1.5-fold molar excess of BG-Ce6 for 2 h, then a 1.5-fold molar excess of BG-VistaGreen. Coupled proteins were separated by SDS-PAGE and visualized with the CRi Maestro Imaging System. The different dye spectra were unmixed using Maestro software and the corresponding gel was stained with Coomassie Brilliant Blue (c).

FIG. 4: Internalization of fusion proteins analyzed by confocal microscopy. Confocal images were obtained for the $EGFR^+$ cell lines A431, MDA-MB-468, MDA-MB-231 and SiHa, and for the $EGFR^-$ cell lines L540 and CHO-K1 incubated with 0.5 µg scFv-425-SNAP-Ce6 for 30 min at 4° C. (a) or for 60 min at 37° C. (b). (1) Ce6 fluorescence signal; (2) transmitted light; (3) overlay of fluorescence signal and transmitted light.

FIG. 5: Evaluation of photodynamic therapeutic efficiency. Cell proliferation and apoptosis assays were carried out using the scFv-425-SNAP-Ce6. The cytotoxicity of scFv-425-BG-Ce6 was determined against cell lines A431 (■), MDA-MB-468 (▲), MDA-MB-231 (♦), SiHa (●) and CHO-K1 (▼) using the XTT assay on (a) irradiated cells and (b) non-irradiated cells. The cytotoxicity scFv-Ki4-SNAP-Ce6 against A431 cells (x) was tested as a control. The same cells were treated with different concentrations of BG-Ce6 and cell viability was analyzed with (c) and without (d) light activation. (e) Apoptosis was evaluated using the Apo-ONE™ Homogeneous Caspase-3/7 Assay, with 50 nM BG-Ce6, 200 nM scFv-SNAP-Ce6 and 200 nM scFv-Ki4-SNAP-Ce6. (f) The generation of reactive oxygen species by illuminating photosensitized A431 cells, detected using the dichlorofluorescein derivative carboxy-H2DCFDA.

Photodynamic therapy (PDT) is a minimally invasive treatment that uses nontoxic photosensitizers and harmless visible light in combination with oxygen to produce cytotoxic reactive oxygen species that kill malignant cells by apoptosis and/or necrosis[12]. Many different photosensitizers have been developed, but Ce6 has been chosen as a model because it has been evaluated extensively in PDT studies and also has advantageous physical and chemical properties. Ce6 has an absorption maximum at 664 nm, which is a good compromise between photon efficacy and cell penetration[13], and the presence of carboxyl groups allows further functionalization[5].

The use of SNAP-tag technology of the present invention provides a unique conjugation site on the antibody, allowing the production of a homogeneous conjugate preparation. The construct of the invention in which the coding sequence of an scFv antibody that binds specifically to EGFR was genetically fused to the hAGT cassette, endows the antibody with a SNAP-tag and therefore allows site-specific conjugation BG-modified substrates, in particular Ce6. This conjugation method can be applied to any antibody-photosensitizer combination as long as the antibody carries the SNAP-tag and the substrate is modified with a BG group.

The conjugation reaction was efficient, allowing the preparation of homogeneous samples of scFv-425-SNAP-Ce6 and scFv-Ki4-SNAP-Ce6. These preparations were tested for their ability to kill tumor cells specifically. It has been found that scFv-425-SNAP-Ce6 selectively killed $EGFR^+$ cells in four human tumor-derived cell lines representing epidermal, breast and cervical carcinomas (A431, MDA-MB-231, MDA-MB468 and SiHa) after exposure to light. The phototoxicity of scFv-425-SNAP-Ce6 was dependent on the presence of EGFR and light, and toxicity was most potent in A431 and MDA-MB468 cells, which express the largest amount of the receptor ($1$-$1.3 \times 10^6$ receptors/cell)[14,15]. The other cells lines expressed less EGFR ($1.3 \times 10^5$ receptors/cell for MDA-MB-231 and $2 \times 10^4$-$2 \times 10^5$ receptors/cell for SiHa)[15,16], and the toxicity of scFv-425-SNAP-Ce6 was concomitantly reduced, although not to the point where the fusion protein would be therapeutically ineffective. This means that scFv-425-SNAP-Ce6 can target a wide range of $EGFR^+$ cells not only those with the highest expression levels. No toxicity was observed when $EGFR^-$ cells (CHO-K1) were exposed to scFv-425-SNAP-Ce6.

It has been previously shown that scFv-425-SNAP accumulates directly in mouse kidneys after injection, and is subsequently detected in the bladder, indicating clearance by renal filtration[10]. Despite the rapid clearance, the accumulation and retention of scFv-425-SNAP in tumor tissue was evidently sufficient to yield very high tumor to background ratio 10 h post-injection.

Figure 1:
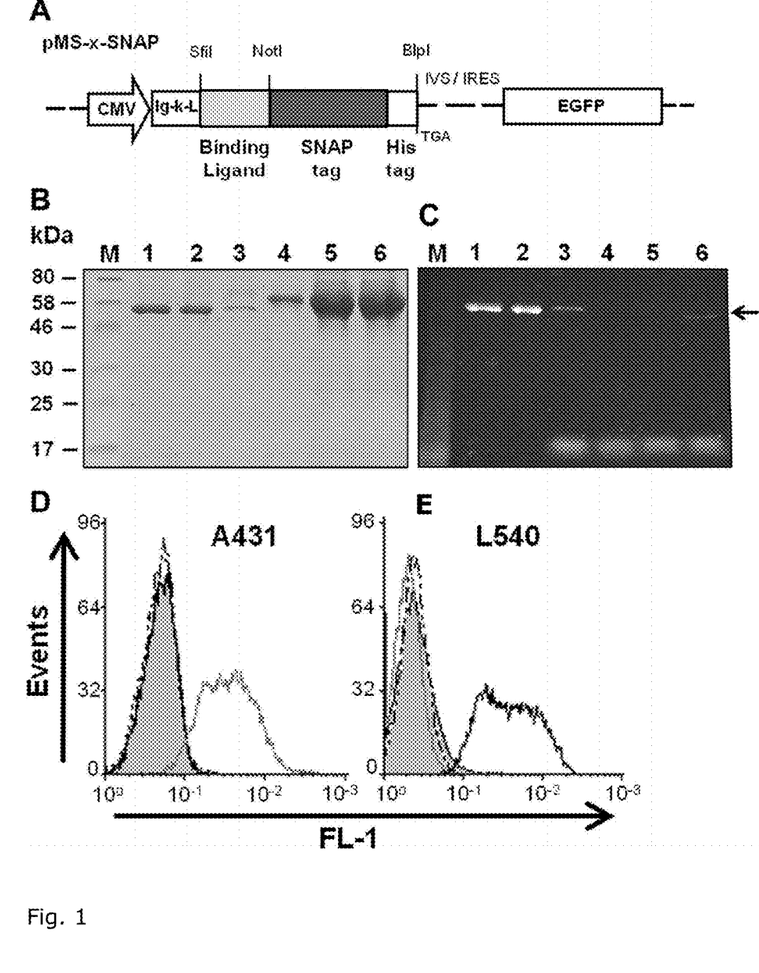

Expression, Purification and Functional Analysis of scFv/SNAP-Tag Fusion Proteins The coding sequences for the EGFR-specific scFv-425 antibody fragment[10] and a control fragment (scFv-Ki4)[17] that binds to a different antigen (CD30) were transferred to the pMS-SNAP bicistronic vector to generate the complete scFv-425-SNAP and scFv-Ki4-SNAP cassettes, as shown in (FIG. 1a). The constructs were introduced into HEK-293T cells by transfection and stably transformed cells were identified by selection on zeocin and by monitoring green fluorescent protein (GFP) activity. The fusion proteins were isolated from the culture supernatant to a final purity of ~90% by affinity chromatography (using the C-terminal His$_6$ tag) and the final yield was 18 mg/L of protein in the supernatant (FIG. 1b).

The activity of the SNAP-tag was confirmed in each of the fusion proteins by mixing the unprocessed culture supernatant, the flow through fraction and the eluate from the chromatography step with BG-modified Vista Green (FIG. 1c). The binding activity of the scFv-425-SNAP protein was confirmed by flow cytometry using one target cell line expressing EGFR (A431), and one control cell line lacking this antigen but expressing CD30 (L540). Binding was detected with a secondary anti-His$_5$ Alexa 488 antibody. Flow cytometry data confirmed the rapid and efficient binding of scFv-425-SNAP specifically to EGFR$^+$ target cells (FIG. 1d), whereas scFv-Ki4/SNAP bound only to the CD30$^+$ L540 cells (FIG. 1e).

Modification of the Photosensitizer Chlorin e6 with Benzylguanine

Figure 2:
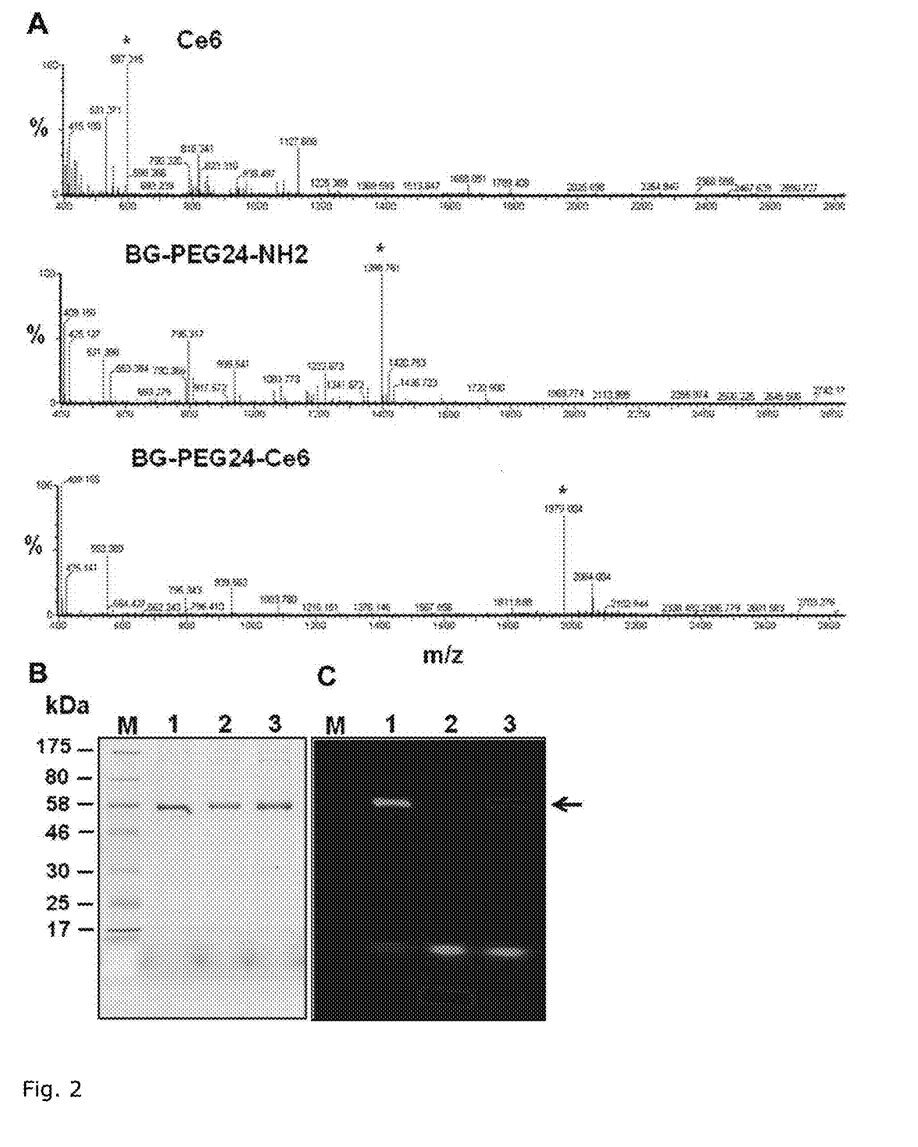

The photosensitizer chlorin e6 (Ce6) was modified successfully using N-(3-dimethylaminopropyl)-N'-ethylcarbodiimide hydrochloride (EDC), the sodium salt of hydroxysulfosuccinimide (sulfo-NHS) and a BG-PEG24-NH$_2$ linker. Ce6 carboxyl groups were modified to BG groups, and the efficiency of the reaction was determined by HPLC (data not shown). The high purity of BG-PEG24-Ce6 was confirmed by mass spectrometry. The accurate masses of Ce6, BG-PEG24-NH$_2$ and BG-PEG24-Ce6 were detected on a Micromass QTOFII mass spectrometer, which confirmed that purified BG-PEG24-Ce6 had the same mass as the theoretical mass calculated for coupled Ce6 and BG-PEG24-NH2 (FIG. 2a)

Protein Labeling with BG-Modified Fluorophores and Ce6

The functionality of the SNAP-tag was tested by coupling to BG-modified fluorescent dye, which revealed a labeling efficiency of 85-90% after a 2-h incubation at room temperature (data not shown). The reaction was repeated using BG-modified Ce6. The photosensitizer reacted solely with the active SNAP-tag in the fusion proteins and the reaction could be irreversibly blocked with the bromothenylpteridine (BTP), as shown by post-incubation with a 1.5-fold molar excess of BG-Vista Green. Analysis with the CRi Maestro imaging system showed no fluorescence associated with the previously blocked fusion protein (FIG. 2b,c).

Flow Cytometry and Confocal Microscopy

Figure 3:
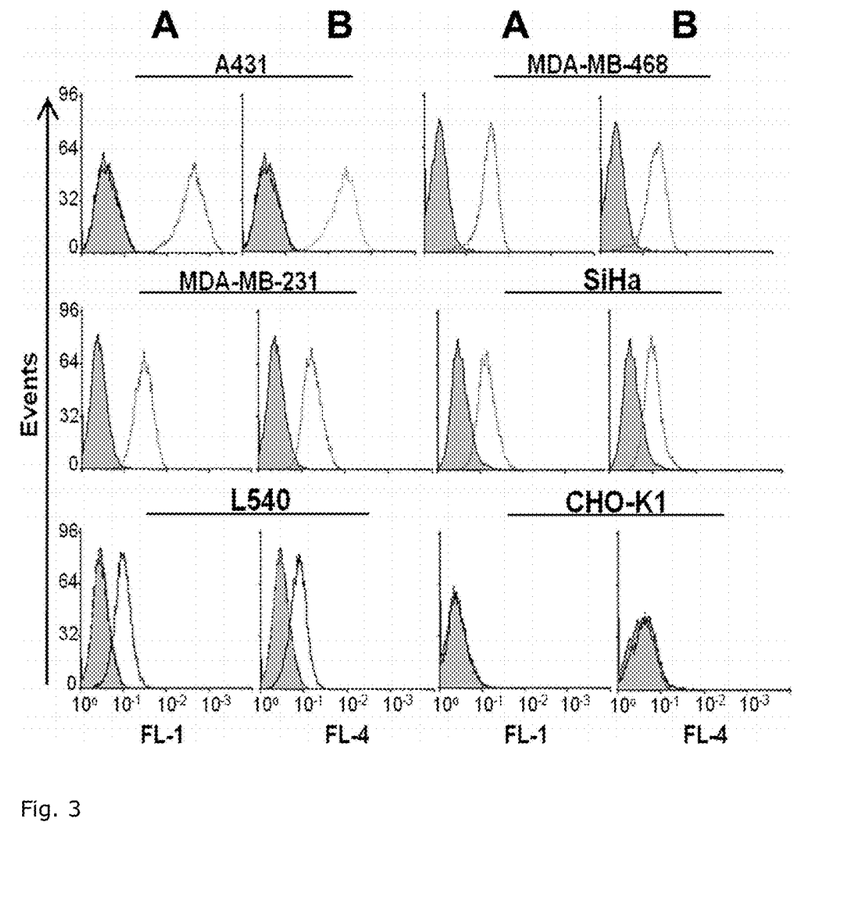
FIG. 3: The binding activities of scFv-425-SNAP-VistaGreen and scFv-425-SNAP-Ce6, which specifically recognize $EGFR^+$ cells. Flow cytometry analysis was carried out after incubating $4 \times 10^5$ cells with each fusion protein for 20 min at 37° C. in PBS. (a) The scFv-425-SNAP-VistaGreen (light gray curve) was tested against A431, MDA-MB-468, MDA-MB-231, SiHa, L540, and CHO-K1 cells (filled gray curve). As a control, scFv-Ki4-SNAP was labeled with BG-VistaGreen (black curve) and its binding activity was tested against A431, L540 and CHO-K1 cells (filled gray curves). (b) The binding efficiency of scFv-425-SNAP-Ce6 (light gray curve) was tested against A431, MDA-MB-468, MDA-MB-231, SiHa, L540 and CHO-K1 cells (filled gray curves). As a control, scFv-Ki4-SNAP labeled with BG-Ce6 (black curve) was tested against A431, L540 and CHO-K1 cells (filled gray curves).

To determine the activity of labeled scFv-425-SNAP fusion proteins, flow cytometry analysis was carried out using proteins that had been labeled with either BG-Vista Green or BG-Ce6. All the labeled proteins showed a strong fluorescence signal on the corresponding target cell line (A431, MDA-MB-231, MDA-MB-468 and SiHa) but not on control cells (L540 and CHO-K1) after a 30-min incubation on ice. As expected, labeled scFv-Ki4-SNAP showed a strong fluorescence signal on L540 but not on A431 and CHO-K1 cells (FIG. 3).

Figure 4:
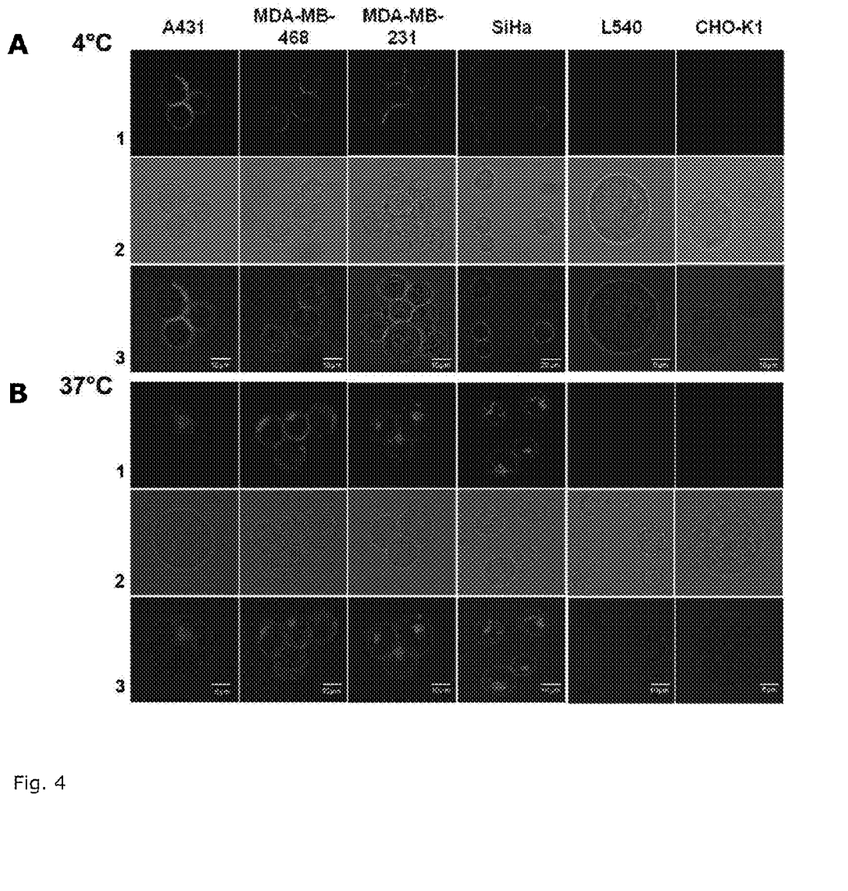

Confocal microscopy revealed strong, specific and homogeneous membrane staining on A431, MDA-MB-231, MDA-MB468 and SiHa cells incubated with scFv-425-SNAP-Ce6 (FIG. 4a). The labeled fusion protein was specifically and efficiently taken up into A431, MDA-MB-231, MDA-MB468 and SiHa cells after a 30-min incubation at 37° C. but not at 4° C. (FIG. 4b). In contrast, no signal was detected when the EGFR$^-$ cell lines L540 and CHO-K1 were incubated with scFv-425-SNAP-Ce6 under the same conditions (FIG. 4a,b).

Photocytotoxicity of scFv-425-SNAP-Ce6

Figure 5:
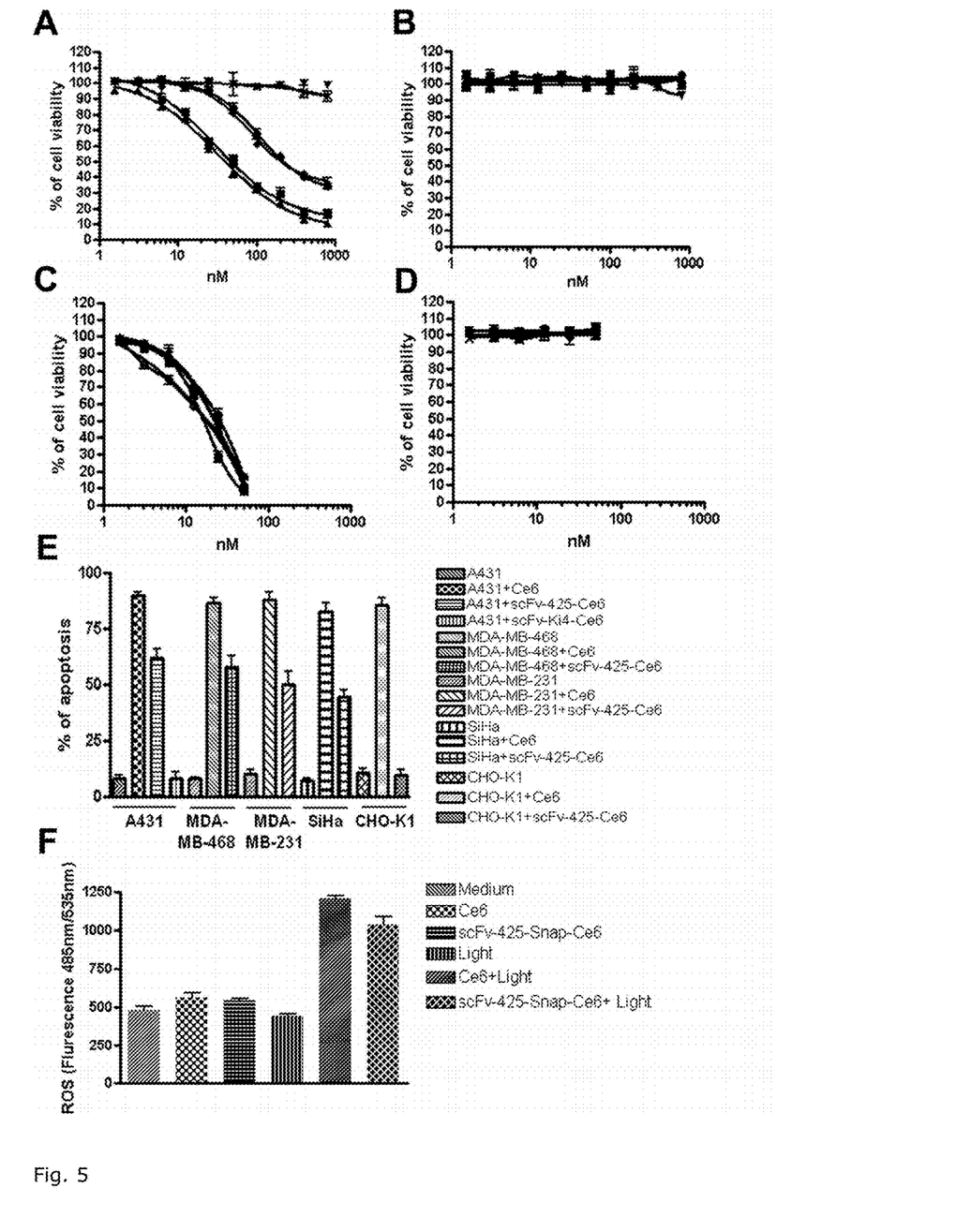

The concentration-dependent cytotoxic effects of scFv-425-SNAP-Ce6 and unconjugated BG-Ce6 were evaluated using an XTT-based colorimetric cell proliferation assay with the four EGFR$^+$ cell lines and CHO-K1 as a negative controls. The viability of A431, MDA-MB-231, MDA-MB-468 and SiHa cells treated with scFv-425-SNAP-Ce6 was reduced significantly, in a concentration-dependent manner, after a 24-h incubation followed the light activation. The IC$_{50}$ values were 48 nM (A431), 200 nM (MDA-MB-231), 38 nM (MDA-MB-468) and 218 nM (SiHa). CHO-K1 cells remained unaffected even when exposed to 800 nM of the conjugated fusion proteins, and the control construct scFv-Ki4-SNAP-Ce6 had a negligible effect in both A431 and CHO-K1 cells. In contrast, unconjugated Ce6 was toxic towards all the cell lines, with IC$_{50}$ values of 16 nM (A431), 22 nM (MDA-MB231), 22 nM (MDA-MB-468), 26 nM (SiHa) and 18 nM (CHO-K1). These data are shown in (FIG. 5a,c).

Both the conjugated and unconjugated forms of Ce6 were toxic only after light activation, as confirmed by carrying out parallel experiments without the light activation step. No significant reduction in viability was observed in any of the cell lines (FIG. 5b,d).

To determine whether scFv-425-SNAP-Ce6 selectively induced programmed cell death in target cells by triggering the apoptotic pathway, the activity of caspase-3 and caspase-7 has been analyzed in A431, MDA-MB-231, MDA-MB468, SiHa and CHO-K1 cells 24 h after light activation. Both scFv-425-SNAP-Ce6 (200 nM) and unconjugated Ce6 (50 nM) increased the levels of caspase-3 and caspase-7, whereas no significant increase was observed in A431 cells treated with 200 nM scFv-Ki4-SNAP-Ce6 (FIG. 5e).

The production of ROS in photoactivated A431 cells was investigated by measuring the 485/535-nm fluorescence of DCF, produced by the oxidation and deacetylation of 6-carboxy-20,70-dichlorodihydrofluoresceindiacetatedi-(acetoxy-methyl)ester (H$_2$DCFDA). It has been found that a burst of ROS synthesis follows light activation in the presence of 200 nM of the conjugated Ce6 and 50 nM of the unconjugated Ce6, but there was only a small increase in ROS levels in non-irradiated cells, barely above the background level observed in cells that were not treated with the photosensitizer (FIG. 5f).

Methods

Cell Culture

All cell lines were of human origin, including the EGFR$^+$ A431, MDA-MB-231, MDA-MB468 and SiHa cells, and the EGFR$^-$ L540, CHO-K1 and HEK-293T cells. A431, L540, CHO-K1 and HEK-293T cells were cultured in RPMI-1640 medium supplemented with 2 mM L-glutamine, 10% (v/v) fetal bovine serum (FBS) and 100 U/ml penicillin-streptomycin. MDA-MB-231, MDA-MB468 and SiHa cells were cultured in DMEM with 10% (v/v) fetal bovine serum (FBS) and 100 U/ml penicillin-streptomycin. All cells were incubated at 37° C. in a 5% $CO_2$ atmosphere. All media and additives were obtained from Invitrogen, Darmstadt, Germany.

Protein Expression and Purification.

The sequence for each scFv was inserted into an expression cassette providing an N-terminal binding ligand (scFv-425 or scFv-Ki4) and a C-terminal O6-alkylguanine-DNA alkyltransferase (SNAP-tag) sequence. The TGA stop codon is generated immediately after $His_6$ tag sequence. $His_6$-tagged fusion proteins were purified from cell-free supernatants by Ni-NTA metal affinity chromatography. Larger volumes were purified on an Akta FLPC system with a 5-mL Ni-NTA Superflow cartridge (Qiagen, Hilden, Germany) after equilibration with 4× buffer (200 mM $NaH_2PO_4$, 1.2 M NaCl, 40 mM imidazole, pH 8). Bound His-tagged proteins were eluted in 50 mM $NaH_2PO_4$, 300 mM NaCl, 250 mM imidazole, pH 8). After elution, proteins were dialyzed at 4° C. overnight against phosphate-buffered saline (PBS) containing 1 mM dithioerythritol (Carl Roth GmBH, Karlsruhe, Germany). Ectoine cryopreservative was added to a final concentration of 50 mM, and aliquots were stored at −20° C.

Modification of Ce6 with Benzylguanine

The carboxyl groups of Ce6 (Porphyrin Products, Logan, Utah), were modified with benzylguanine by mixing 2 mg Ce6 in dimethylformamide for 30 min at room temperature with a five-fold molar excess of EDC and sulfo-NHS (Sigma-Aldrich, St Louis, Mo.). The activated mixture was then mixed with a four-fold molar excess of the benzylguanine linker BG-PEG24-$NH_2$ (Covalys Biosciences AG, Witterswil, Switzerland) in the dark at room temperature overnight. The modified Ce6 was purified by HPLC using a Shimadzu Prominence HPLC system, and a 2.5 µm (4.6×50 mm) Water XBridge™ $OSTC_{18}$ column (Waters, Milford, Mass.) at a flow rate was 1 mL/min. Separations were carried out using a 20-min gradient from 100% 0.1 M TEAA to 100% acetonitrile, monitored at 280 and 410 nm. The masses of Ce6, BG-PEG24-NH2 and BG-PEG24-Ce6 were confirmed using a Micromass QTOFII mass spectrometer with an electrospray ion source Advion Nanomate (Advion, Ithaca, N.Y., USA) 7 µl sample volume, 1.4 kV. Accurate masses were derived from mass spectra in the range 300-2500 m/z using the MaxEnt3™ algorithm (Micromass) in the range of 400-2000 Da.

Protein Labeling

The purified SNAP-tag fusion proteins were conjugated with BG-modified dyes (Covalys Biosciences AG, Witterswil, Switzerland) or BG-modified Ce6 by incubation in the dark with a 1.5-3-fold molar excess of dye for 2 h at room temperature. Residual dye was removed by gel filtration chromatography using zeba spin desalting columns, 7K MWCO (Thermo Fisher Scientific, Rockford, Ill.). Coupling efficiency was determined photometrically using the extinction coefficients of the corresponding dyes and the theoretical extinction coefficient of the fusion proteins. Labeled proteins were visualized after separation by SDS-PAGE with either a UV transilluminator Gel Doc XR gel documentation (Bio-Rad Laboratories, München, Germany) or a CRi Maestro imaging system (CRi, Woburn, Mass., USA) using the blue and yellow filter sets.

Flow Cytometry

The binding efficiency of the labeled and unlabeled fusion proteins was determined by flow cytometry using a FACSCalibur (Becton & Dickinson, Heidelberg, Germany) and CellQuest software. $EGFR^+$ cell lines A431, MDA-MB-231, MDA-MB468 and SiHa were used to test the binding efficiency of scFv-425-SNAP, and $EGFR^-$ cell lines L540 and CHO-K1 were used as negative controls. The control fusion protein scFv-Ki4-SNAP recognizes the antigen CD30 and should therefore bind to L540 cells but not to the other cell lines. Approximately $4×10^5$ cells were incubated in 200 µL PBS containing 0.5 µg of labeled protein for 20 min on ice. The cells were then washed twice with 1.8 mL PBS in a conventional cell washer and analyzed by flow cytometry.

Confocal Microscopy

Images were visualized with a TCS SP5 confocal microscope (LEICA Microsystem, Wetzlar, Germany). Cells were prepared as described above for flow cytometry. Binding efficiency was determined by incubating cells with the labeled fusion proteins for 30 min on ice. Internalization was monitored by incubating cells with the labeled fusion proteins for 30 min at 37° C.

Phototoxicity of scFv-425-SNAP-Ce6

Aliquots of A431, MDA-MB-231, MDA-MB468, SiHa and CHO-K1 cells ($2×10^4$) cultured as described above were washed twice in PBS and then treated with increasing concentrations of either Ce6, scFv-425-SNAP-Ce6 or Ki4-scFv/SNAP-Ce6 followed by incubation for 3 h at 37° C. Control cultures were incubated with 500 µg/ml zeocin instead of the photosensitizer. The cells were then irradiated with 24 $J/cm^2$ broadband visible/near infrared light using Hydrosun type 505, 7-mm water cuvette and orange filter OG590, spectrum in the range 580-1400 nm (Hydrosun Medizintechnik GmbH, Müllheim, Germany) and incubated for a further 24 h at 37° C. in a 5% $CO_2$ atmosphere.

Cell viability was determined using the XTT cell proliferation kit II (Roche, Mannheim Germany), 24 h after light activation. Cells were incubated with 2,3-bis(2-methoxy-4-nitro-5sulphonyl)-5[(phenyl-amino)carbonyl]-2H-tetrazolium hydroxide reagent (1 mg/ml), and incubated for 2 h at 37° C. Reduction of XTT to formazan by viable tumor cells was monitored colorimetrically at an absorbance wavelength of 450 nm and a reference wavelength of 630 nm using an ELISA plate reader Elisareader ELx808 (Bio-TEK, Bad Friedrichsahll, Germany).

Caspase-3/7 activity in cell lysates was determined using the Apo-ONE Caspase-3/7 assay (Promega, Mannheim, Germany) 24 h after light activation. Briefly, 100 µl of Apo-ONE reagent was added to the cells, and they were incubated for 6 h before fluorescence readings were taken with an ELISA plate reader Elisareader ELx808 (Bio-TEK, Bad Friedrichsahll, Germany) using an excitation wavelength of 485 nm and an emission wavelength of 535 nm. The concentration of ROS was determined by measuring the 485/535 nm fluorescence ratio of H2DCFDA (Invitrogen, Darmstadt, Germany). Briefly, $2×10^4$ cells were incubated in the presence of 50 nM Ce6 or 200 nM scFv-425-SNAP-Ce6 and 10 µM $H_2DCFDA$ for 30 min in PBS containing 1% FCS. The cells were washed twice with warm PBS containing 2.5% FCS, cultured for 2 h in RPMI-160 medium and illuminated as described above. Fluorescence readings were taken directly after illumination. A blank probe (cells and medium) reading was used as the background and subtracted from all the sample readings.

Data Analysis

Statistical analysis and curve fitting were performed with GraphPad Prism software (GraphPad, San Siego, Calif.). Data are presented as the mean±MES. Student's t test and two-way analysis of variance were used to assess the significance of independent experiments. The criterion $p<0.05$ was used to determine statistical significance.

REFERENCES

1. Huang, Z. A Review of Progress in Clinical Photodynamic Therapy. Technol Cancer Res Treat. 4, 283-293 (2005).
2. Palumbo, G. Photodynamic therapy and cancer: a brief sightseeing tour. Expert Opin. Drug Deliv. 4, 131-148 (2007).
3. Castano, A. P, Demidova, T. N. & Hamblin, M. R. Mechanisms in photodynamic therapy: part one-photosensitizers, photochemistry and cellular localization. Photodiagnosis and Photodynamic Therapy 1, 279-293 (2004).
4. Olivo, M., Bhuvaneswari, R., Lucky, S. S., Dendukuri, N. & Thong, P. S. Targeted Therapy of Cancer Using Photodynamic Therapy in Combination with Multifaceted Anti-Tumor Modalities. Pharmaceuticals 3, 1507-1529 (2010).
5. Van Dongen, G. A. M. S., Visser, G. W. M. & Vrouenraets, M. B. Photosensitizer-antibody conjugates for detection and therapy of cancer. Adv. Drug. Delivery. Rev. 56, 31-52 (2004).
6. Jeger, S. et al. Site-Specific and Stoichiometric Modification of Antibodies by Bacterial Transglutaminase. Angew. Chem. Int. Ed. 49, 9995-9997 (2010).
7. Adams, G. P. & Weiner, L. M. Monoclonal antibody therapy of cancer. Nat. Biotechnol. 23, 1147-1157 (2005).
8. Junutula, J. R. et al. Site-specific conjugation of a cytotoxic drug to an antibody improves the therapeutic index. Nat. Biotechnol. 26, 925-932 (2008).
9. Hamblett, K. J. et al. Effects of drug loading on the antitumor activity of a monoclonal antibody drug conjugate. Clin. Cancer Res. 10, 7063-7070 (2004).
10. Kampmeier, F. et al. Rapid optical imaging of EGF receptor expression with a single-chain antibody SNAP-tag fusion protein. Eur. J. Nucl. Med. Mol. Imaging 37, 1926-1934 (2010).
11. Gronemeyer, T., Chidley, C., Juillerat, A., Heinis, C. & Johnsson, K. Directed evolution of O6-alkylguanine-DNA alkyltransferase for applications in protein labeling. PEDS 19, 309-16 (2006).
12. Bhatti, M. et al. Targeted photodynamic therapy with multiply-loaded recombinant antibody fragments. Int J Cancer 1, 122:1155-63 (2008).
13. Douillard, S., Olivier, D. & Patrice, T. In vitro and in vivo evaluation of Radachlorin® sensitizer for photodynamic therapy. Photochem Photobiol. Sci 8, 405-413 (2009).
14. Gamou, S., Kim, Y. S. & Shimizu, N. Different responses to EGF in two human carcinoma cell lines, A431 and UCVA-1, possessing high numbers of EGF receptors. Mol. Cell. Endocrinol. 37, 205-213 (1986).
15. Cai, K. et al. Relationship between induction of phosphorylated H2AX and survival in breast cancer cells exposed to $^{111}$In-DTPA-hEGF. J Nucl Med. 49, 1353-1361 (2008).
16. Nida, D. L., Rahman, M. S., Carlson, K. D., Richards-Kortum, R. & Follen, M. Fluorescent nanocrystals for use in early cervical cancer detection. Gynecologic Oncology 99, 89-94 (2005).
17. Kampmeier, F. et al. Site-specific, covalent labeling of recombinant antibody fragments via fusion to an engineered version of 6-Oalkylguanine DNA alkyltransferase. Bioconjug Chem. 20, 1010-1015 (2009).

---

The invention claimed is:

1. A compound comprising:
a photosensitizer covalently coupled to
a binding protein selected from the group consisting of an antibody or its antigen-binding fragment thereof; and
wherein the binding protein binds a growth factor receptor,
the photosensitizer is coupled to the binding protein via O6-alkylguanine-DNA alkyltransferase (hAGTm), a modified human DNA repair protein, and
wherein the binding protein comprising the amino acid sequence of SEQ ID NO: 1 or SEQ ID NO: 3.

2. The compound of claim 1, wherein the photosensitizer is coupled at the active site of the O6-alkylguanine-DNA alkyltransferase.

3. The compound of claim 1, wherein the photosensitizer is selected from the group consisting of porphyrins, chlorophylls and dyes.

4. The compound of claim 1, specifically targeting an internalizing and disease-specific cell surface receptor.

5. The compound of claim 1, wherein the binding protein is an scFv antibody.

6. A compound comprising:
a binding protein comprising the amino acid sequence of SEQ ID NO: 1 or SEQ ID NO: 3,
wherein the binding protein binds a growth factor receptor, and
wherein the binding protein is covalently coupled to a modified human DNA repair protein called O6-alkylguanine-DNA alkyltransferase (hAGTm).

7. The compound of claim 6, wherein the binding protein is encoded by the polynucleotide sequence of SEQ ID NO: 2 or SEQ ID NO: 4.

8. A compound comprising:
a photosensitizer covalently coupled to
a binding protein comprising a protein encoded by a polynucleotide having the nucleotide sequence of SEQ ID NO: 5;
wherein the binding protein binds a growth factor receptor, and
wherein the photosensitizer is coupled to the binding protein via O6-alkylguanine-DNA alkyltransferase (hAGTm), a modified human DNA repair protein.

9. A method for manufacturing the compound of claim 1 comprising the step of fusing O6-alkylguanine-DNA alkyltransferase (hAGTm) with the binding protein comprising the amino acid sequence of SEQ ID NO: 1 or SEQ ID NO: 3 to form a fusion protein.

10. The method of claim 9 wherein the binding protein encoded by the nucleotide sequence of SEQ ID NO: 2 or SEQ ID NO: 4 is inserted into a SifI and NotI-digested site of eukaryotic expression vector pMS-SNAP providing an N-terminal binding ligand and a C-terminal SNAP-tag sequence.

11. The method of claim 9 wherein the fusion protein is expressed in human embryonic kidney cell line.

12. The method of claim 9 wherein the fusion protein is purified from cell-free supernatant by an affinity chromatography.

13. The compound of claim 1, wherein the photosensitizer is a porphyrin derivative of the formula 14. A method of manufacturing the compound of claim 13, comprising reacting the carboxyl groups of the porphyrin derivative with an activated ester or a coupling agent, followed by reacting with O6-benzylguanine, O2-benzylcytosine or a coenzyme A (CoA).

15. The method of claim 14, wherein O6-benzylguanine, O2-benzylcytosine or CoA is coupled to a linker molecule and/or the activated ester is formed by succinimides, or the coupling agent is a carbodiimide.

16. A medicament comprising the compound of claim 1 and a pharmaceutically acceptable adjuvant for improving or rendering a pharmaceutical effect associated with photoimmunotherapy.

17. A method for treating cancer in a subject by photoimmunotherapy, comprising administering to the subject the compound of claim 1.

18. The compound of claim 1, wherein the binding protein is scFv.

19. The compound of claim 1, wherein the growth factor receptor is a tyrosine kinase growth factor receptor of the ErbB family.

20. The compound of claim 1, wherein the binding protein is encoded by the polynucleotide sequence of SEQ ID NO: 2 or SEQ ID NO: 4.

21. The compound of claim 6, wherein the binding protein is scFv.

22. The compound of claim 6, wherein the growth factor receptor is a tyrosine kinase growth factor receptor of the ErbB family.

* * * * *

SEQUENCE LISTING

<160> NUMBER OF SEQ ID NOS: 5

<210> SEQ ID NO 1
<211> LENGTH: 245
<212> TYPE: PRT
<213> ORGANISM: Unknown
<220> FEATURE:
<223> OTHER INFORMATION: fusion protein

<400> SEQUENCE: 1

```
Met Ala Gln Val Gln Leu Gln Gln Ser Gly Ala Glu Leu Val Lys Pro
1               5                   10                  15

Gly Ala Ser Val Lys Leu Ser Cys Lys Ala Ser Gly Tyr Thr Phe Thr
            20                  25                  30

Ser His Trp Met His Trp Val Lys Gln Arg Ala Gly Gln Gly Leu Glu
        35                  40                  45

Trp Ile Gly Glu Phe Asn Pro Ser Asn Gly Arg Thr Asn Tyr Asn Glu
    50                  55                  60

Lys Phe Lys Ser Lys Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
            85                  90                  95

Tyr Cys Ala Ser Arg Asp Tyr Asp Tyr Asp Gly Arg Tyr Phe Asp Tyr
            100                 105                 110

Trp Gly Gln Gly Thr Thr Val Thr Val Ser Ser Gly Gly Gly Gly Ser
        115                 120                 125

Gly Gly Gly Gly Ser Gly Gly Gly Ser Asp Ile Glu Leu Thr Gln
    130                 135                 140
```

Ser Pro Ala Ile Met Ser Ala Ser Pro Gly Glu Lys Val Thr Met Thr
145                 150                 155                 160

Cys Ser Ala Ser Ser Val Thr Tyr Met Tyr Trp Tyr Gln Gln Lys
            165                 170                 175

Pro Gly Ser Ser Pro Arg Leu Leu Ile Tyr Asp Thr Ser Asn Leu Ala
        180                 185                 190

Ser Gly Val Pro Val Arg Phe Ser Gly Ser Gly Ser Gly Thr Ser Tyr
            195                 200                 205

Ser Leu Thr Ile Ser Arg Met Glu Ala Glu Asp Ala Ala Thr Tyr Tyr
        210                 215                 220

Cys Gln Gln Trp Ser Ser His Ile Phe Thr Phe Gly Ser Gly Thr Glu
225                 230                 235                 240

Leu Glu Ile Lys Arg
            245

<210> SEQ ID NO 2
<211> LENGTH: 737
<212> TYPE: DNA
<213> ORGANISM: Unknown
<220> FEATURE:
<223> OTHER INFORMATION: coding for fusion protein

<400> SEQUENCE: 2
atggcgcagg tgcaactgca gcagtctggg gctgaactgg tgaagcctgg ggcttcagtg     60
aagttgtcct gcaaggcttc cggctacacc ttcaccagcc actggatgca ctgggtgaag    120
cagagggctg gacaaggcct tgagtggatc ggagagttta tcccagcaa cggccgtact    180 aactacaatg agaaattcaa gagcaaggcc acactgactg tagacaaatc ctccagcaca    240
gcctacatgc aactcagcag cctgacatct gaggactctg cggtctatta ctgtgccagt    300
cgggactatg attacgacgg acggtacttt gactactggg gccaagggac cacggtcacc    360
gtctcctcag gtggcggtgg ctcgggcggt ggtgggtcgg gtggcggcgg atctgacatc    420
gagctcaccc agtctccagc aatcatgtct gcatctccag gggagaaggt cactatgacc    480
tgcagtgcca gctcaagtgt aacttacatg tattggtacc agcagaagcc aggatcctcc    540
cccagactcc tgatttatga cacatccaac ctggcttctg gagtccctgt tcgtttcagt    600
ggcagtgggt ctgggacctc ttactctctc acaatcagcc gaatggaggc tgaagatgct    660
gccacttatt actgccagca gtggagtagt cacatattca cgttcggctc ggggacagaa    720
ctcgagatca aacgggc                                                    737

<210> SEQ ID NO 3
<211> LENGTH: 465
<212> TYPE: PRT
<213> ORGANISM: Unknown
<220> FEATURE:
<223> OTHER INFORMATION: fusion protein

<400> SEQUENCE: 3

Met Ala Gln Val Gln Leu Gln Gln Ser Gly Ala Glu Leu Val Lys Pro
1               5                   10                  15

Gly Ala Ser Val Lys Leu Ser Cys Lys Ala Ser Gly Tyr Thr Phe Thr
            20                  25                  30

Ser His Trp Met His Trp Val Lys Gln Arg Ala Gly Gln Gly Leu Glu
        35                  40                  45

Trp Ile Gly Glu Phe Asn Pro Ser Asn Gly Arg Thr Asn Tyr Asn Glu
    50                  55                  60

```
Lys Phe Lys Ser Lys Ala Thr Leu Thr Val Asp Lys Ser Ser Thr
 65                  70                  75                  80

Ala Tyr Met Gln Leu Ser Ser Leu Thr Ser Glu Asp Ser Ala Val Tyr
                 85                  90                  95

Tyr Cys Ala Ser Arg Asp Tyr Asp Tyr Asp Gly Arg Tyr Phe Asp Tyr
            100                 105                 110

Trp Gly Gln Gly Thr Thr Val Thr Val Ser Ser Gly Gly Gly Gly Ser
            115                 120                 125

Gly Gly Gly Gly Ser Gly Gly Gly Ser Asp Ile Glu Leu Thr Gln
        130                 135                 140

Ser Pro Ala Ile Met Ser Ala Ser Pro Gly Glu Lys Val Thr Met Thr
145                 150                 155                 160

Cys Ser Ala Ser Ser Ser Val Thr Tyr Met Tyr Trp Tyr Gln Gln Lys
                165                 170                 175

Pro Gly Ser Ser Pro Arg Leu Leu Ile Tyr Asp Thr Ser Asn Leu Ala
                180                 185                 190

Ser Gly Val Pro Val Arg Phe Ser Gly Ser Gly Ser Gly Thr Ser Tyr
            195                 200                 205

Ser Leu Thr Ile Ser Arg Met Glu Ala Glu Asp Ala Ala Thr Tyr Tyr
210                 215                 220

Cys Gln Gln Trp Ser Ser His Ile Phe Thr Phe Gly Ser Gly Thr Glu
225                 230                 235                 240

Leu Glu Ile Lys Arg Ala Ala Ala Gly Gly Gly Gly Ser Ala Leu Ala
                245                 250                 255

Leu Pro Leu Ser Ser Ile Phe Ser Arg Ile Gly Asp Pro Gly Gly Pro
                260                 265                 270

Tyr Val His Asp Glu Val Asp Arg Gly Pro Pro Gly Ser Arg Met Asp
            275                 280                 285

Lys Asp Cys Glu Met Lys Arg Thr Thr Leu Asp Ser Pro Leu Gly Lys
290                 295                 300

Leu Glu Leu Ser Gly Cys Glu Gln Gly Leu His Glu Ile Lys Leu Leu
305                 310                 315                 320

Gly Lys Gly Thr Ser Ala Ala Asp Ala Val Glu Val Pro Ala Pro Ala
                325                 330                 335

Ala Val Leu Gly Gly Pro Glu Pro Leu Met Gln Ala Thr Ala Trp Leu
            340                 345                 350

Asn Ala Tyr Phe His Gln Pro Glu Ala Ile Glu Glu Phe Pro Val Pro
            355                 360                 365

Ala Leu His His Pro Val Phe Gln Gln Glu Ser Phe Thr Arg Gln Val
            370                 375                 380

Leu Trp Lys Leu Leu Lys Val Val Lys Phe Gly Glu Val Ile Ser Tyr
385                 390                 395                 400

Gln Gln Leu Ala Ala Leu Ala Gly Asn Pro Ala Ala Thr Ala Ala Val
                405                 410                 415

Lys Thr Ala Leu Ser Gly Asn Pro Val Pro Ile Leu Ile Pro Cys His
            420                 425                 430

Arg Val Val Ser Ser Ser Gly Ala Val Gly Gly Tyr Glu Gly Gly Leu
            435                 440                 445

Ala Val Lys Glu Trp Leu Leu Ala His Glu Gly His Arg Leu Gly Lys
            450                 455                 460

Pro
465
```

<210> SEQ ID NO 4
<211> LENGTH: 1411
<212> TYPE: DNA
<213> ORGANISM: Unknown
<220> FEATURE:
<223> OTHER INFORMATION: coding for fusion protein

<400> SEQUENCE: 4

| | | | | | |
|---|---|---|---|---|---|
| atggcgcagg | tgcaactgca | gcagtctggg | gctgaactgg | tgaagcctgg | ggcttcagtg | 60 |
| aagttgtcct | gcaaggcttc | cggctacacc | ttcaccagcc | actggatgca | ctgggtgaag | 120 |
| cagagggctg | acaaggcct | tgagtggatc | ggagagttta | atcccagcaa | cggccgtact | 180 |
| aactacaatg | agaaattcaa | gagcaaggcc | acactgacta | gacaaaatc | ctccagcaca | 240 |
| gcctacatgc | aactcagcag | cctgacatct | gaggactctg | cggtctatta | ctgtgccagt | 300 |
| cgggactatg | attacgacgg | acggtacttt | gactactggg | gccaagggac | cacggtcacc | 360 |
| gtctcctcag | gtggcggtgg | ctcgggcggt | ggtgggtcgg | gtggcggcgg | atctgacatc | 420 |
| gagctcaccc | agtctccagc | aatcatgtct | gcatctccag | gggagaaggt | cactatgacc | 480 |
| tgcagtgcca | gctcaagtgt | aacttacatg | tattggtacc | agcagaagcc | aggatcctcc | 540 |
| cccagactcc | tgatttatga | cacatccaac | ctggcttctg | gagtccctgt | tcgtttcagt | 600 |
| ggcagtgggt | ctgggacctc | ttactctctc | acaatcagcc | gaatggaggc | tgaagatgct | 660 |
| gccacttatt | actgccagca | gtggagtagt | cacatattca | cgttcggctc | ggggacagaa | 720 |
| ctcgagatca | aacgggcggc | cgctggaggt | ggaggcagcg | cgctggcgct | gcccttatcg | 780 |
| tcaatcttct | cgcgcattgg | ggaccctggg | ggccgtatg | ttcacgatga | agtcgatcgt | 840 |
| ggtcctcccg | gtctagaat | ggacaaagac | tgcgaaatga | agcgcaccac | cctggatagc | 900 |
| cctctgggca | gctggaact | gtctgggtgc | gaacagggcc | tgcacgagat | caagctgctg | 960 |
| ggcaaaggaa | catctgccgc | cgacgccgtg | gaagtgcctg | ccccagccgc | cgtgctgggc | 1020 |
| ggaccagagc | cactgatgca | ggccaccgcc | tggctcaacg | cctactttca | ccagcctgag | 1080 |
| gccatcgagg | agttccctgt | gccagccctg | caccacccag | tgttccagca | ggagagcttt | 1140 |
| acccgccagt | gctgtggaa | actgctgaaa | gtggtgaagt | tcggagaggt | catcagctac | 1200 |
| cagcagctgg | cggccctggc | gggcaatccc | gccgccaccg | ccgccgtgaa | aaccgccctg | 1260 |
| agcggaaatc | ccgtgcccat | tctgatcccc | tgccaccggg | tggtgtctag | ctctggcgcc | 1320 |
| gtgggggct | acgagggcgg | gctcgccgtg | aaagagtggc | tgctggccca | cgagggccac | 1380 |
| agactgggca | gcctgggct | gggcgctgag | c | | | 1411 |

<210> SEQ ID NO 5
<211> LENGTH: 3263
<212> TYPE: DNA
<213> ORGANISM: Unknown
<220> FEATURE:
<223> OTHER INFORMATION: coding for fusion protein

<400> SEQUENCE: 5

| | | | | | |
|---|---|---|---|---|---|
| gctagccacc | atggagacag | acacactcct | gctatgggta | ctgctgctct | gggttccagg | 60 |
| ttccactggt | gacgcggccc | agccggccat | ggcgcaggtg | caactgcagc | agtctggggc | 120 |
| tgaactggtg | aagcctgggg | cttcagtgaa | gttgtcctgc | aaggcttccg | gctacacctt | 180 |
| caccagccac | tggatgcact | gggtgaagca | gaggctgga | caaggccttg | agtggatcgg | 240 |
| agagtttaat | cccagcaacg | gccgtactaa | ctacaatgag | aaattcaaga | gcaaggccac | 300 |
| actgactgta | gacaaatcct | ccagcacagc | ctacatgcaa | ctcagcagcc | tgacatctga | 360 |

```
ggactctgcg gtctattact gtgccagtcg ggactatgat tacgacggac ggtactttga    420 ctactgggc  caagggacca cggtcaccgt ctcctcaggt ggcggtggct cgggcggtgg    480
tgggtcgggt ggcggcggat ctgacatcga gctcacccag tctccagcaa tcatgtctgc    540
atctccaggg gagaaggtca ctatgacctg cagtgccagc tcaagtgtaa cttacatgta    600
ttggtaccag cagaagccag gatcctcccc cagactcctg atttatgaca catccaacct    660
ggcttctgga gtccctgttc gtttcagtgg cagtgggtct gggacctctt actctctcac    720
aatcagccga atggaggctg aagatgctgc cacttattac tgccagcagt ggagtagtca    780
catattcacg ttcggctcgg ggacagaact cgagatcaaa cgggcggccg ctggaggtgg    840
aggcagcgcg ctggcgctgc ccttatcgtc aatcttctcg cgcattgggg accctggggg    900
cccgtatgtt cacgatgaag tcgatcgtgg tcctcccggg tctagaatgg acaaagactg    960
cgaaatgaag cgcaccaccc tggatagccc tctgggcaag ctggaactgt ctgggtgcga   1020
acagggcctg cacgagatca agctgctggg caaaggaaca tctgccgccg acgccgtgga   1080
agtgcctgcc ccagccgccg tgctgggcgg accagagcca ctgatgcagg ccaccgcctg   1140
gctcaacgcc tactttcacc agcctgaggc catcgaggag ttccctgtgc agccctgca    1200 ccacccagtg ttccagcagg agagctttac ccgccaggtg ctgtggaaac tgctgaaagt   1260
ggtgaagttc ggagaggtca tcagctacca gcagctggcg ccctggcgg  gcaatcccgc   1320 cgccaccgcc gccgtgaaaa ccgccctgag cggaaatccc gtgcccattc tgatcccctg   1380
ccaccggggt gtgtctagct ctggcgccgt ggggggctac gagggcgggc tcgccgtgaa   1440
agagtggctg ctggcccacg agggccacag actgggcaag cctgggctgg gcgctgagca   1500
cgaatttcga ggagggcccg aacaaaaact catctcagaa gaggatctga atagcgccgt   1560
cgaccatcat catcatcatc attgagtttt gagcacgaat tctggaatta attcgctgtc   1620
tgcgagggcc agctgttggg gtgagtactc cctctcaaaa gcgggcatga cttctgcgct   1680
aagattgtca gtttccaaaa acgaggagga tttgatattc acctggcccg cggtgatgcc   1740
tttgagggtg gccgcgtcca tctggtcaga aaagacaatc ttttgttgt  caagcttgag   1800 gtgtggcagg cttgagatct ggccatacac ttgagtgaca atgacatcca ctttgccttt   1860
ctctccacag gtgtccactc ccaggtccaa ctgcaggtcg agcatgcatc tagggcggcc   1920
aattccgccc ctctccctcc ccccccccta acgttactgg ccgaagccgc ttggaataag   1980
gccggtgtgc gtttgtctat atgtgatttt ccaccatatt gccgtctttt ggcaatgtga   2040
gggcccggaa acctggccct gtcttcttga cgagcattcc taggggtctt tcccctctcg   2100
ccaaaggaat gcaaggtctg ttgaatgtcg tgaaggaagc agttcctctg gaagcttctt   2160
gaagacaaac aacgtctgta cgacccttt  gcaggcagcg gaaccccca  cctggcgaca   2220 ggtgcctctg cggccaaaag ccacgtgtat aagatacacc tgcaaaggcg gcacaacccc   2280
agtgccacgt tgtgagttgg atagttgtgg aaagagtcaa atggctctcc tcaagcgtat   2340
tcaacaaggg gctgaaggat gcccagaagg tacccattg  tatgggatct gatctggggc   2400
ctcggtgcac atgctttaca tgtgtttagt cgaggttaaa aaaacgtcta ggccccccga   2460
accacgggga cgtggttttc ctttgaaaaa cacgatgata agcttgccac aacccggat    2520 ccaccggtcg ccaccatggt gagcaagggc gaggagctgt tcaccggggt ggtgcccatc   2580
ctggtcgagc tggacggcga cgtaaacggc cacaagttca gcgtgtccgg cgagggcgag   2640
ggcgatgcca cctacggcaa gctgaccctg aagttcatct gcaccaccgg caagctgccc   2700
```

```
gtgccctggc ccaccctcgt gaccaccctg acctacggcg tgcagtgctt cagccgctac    2760
cccgaccaca tgaagcagca cgacttcttc aagtccgcca tgcccgaagg ctacgtccag    2820
gagcgcacca tcttcttcaa ggacgacggc aactacaaga cccgcgccga ggtgaagttc    2880
gagggcgaca ccctggtgaa ccgcatcgag ctgaagggca tcgacttcaa ggaggacggc    2940
aacatcctgg ggcacaagct ggagtacaac tacaacagcc acaacgtcta tatcatggcc    3000
gacaagcaga agaacggcat caaggtgaac ttcaagatcc gccacaacat cgaggacggc    3060
agcgtgcagc tcgccgacca ctaccagcag aacacccca tcggcgacgg ccccgtgctg     3120
ctgcccgaca accactacct gagcacccag tccgccctga gcaaagaccc caacgagaag    3180
cgcgatcaca tggtcctgct ggagttcgtg accgccgccg ggatcactct cggcatggac    3240
gagctgtaca agtaagttta aac                                           3263
```